(12) United States Patent
Halaka

(10) Patent No.: US 6,562,573 B2
(45) Date of Patent: May 13, 2003

(54) MATERIALS AND METHODS FOR THE PURIFICATION OF POLYELECTROLYTES, PARTICULARLY NUCLEIC ACIDS

(76) Inventor: Folim G. Halaka, 3322 Berwyn #116, North Chicago, IL (US) 60064

( * ) Notice: Subject to any disclaimer, the term of this patent is extended or adjusted under 35 U.S.C. 154(b) by 0 days.

(21) Appl. No.: 09/840,570

(22) Filed: Apr. 23, 2001

(65) Prior Publication Data

US 2001/0041795 A1 Nov. 15, 2001

Related U.S. Application Data

(63) Continuation-in-part of application No. 09/238,343, filed on Jan. 27, 1999, which is a continuation-in-part of application No. 07/772,346, filed on Oct. 7, 1991, now abandoned.

(51) Int. Cl.[7] ............................. C12Q 1/68; C12P 19/34; C07C 7/00; C07H 21/04
(52) U.S. Cl. ........................... 435/6; 435/91.1; 585/800; 536/24.31; 536/24.33
(58) Field of Search .................... 435/6, 91.1; 585/800; 536/24.31, 24.33

(56) References Cited

U.S. PATENT DOCUMENTS

| 4,335,017 A | 6/1982 | Miles et al. ................. 252/430 |
| 4,724,207 A | 2/1988 | Hou et al. ................... 435/180 |
| 4,752,459 A | 6/1988 | Pepper ........................ 423/338 |
| 5,019,232 A | 5/1991 | Wilson et al. .............. 204/182 |
| 5,581,349 A | 12/1996 | Halaka ........................ 356/336 |
| 5,876,937 A | * 3/1999 | Sillekens ....................... 435/6 |

* cited by examiner

Primary Examiner—W. Gary Jones
Assistant Examiner—Arun K Chakrabarti
(74) Attorney, Agent, or Firm—Olson & Hierl, Ltd.

(57) ABSTRACT

This invention describes materials and methods usable for the purification of polyelectrolytes, such as nucleic acids and proteins. The materials of the invention are separation media that possess pH-dependent groups with pKa value in the range of about 5 to about 7. Separation of the nucleic acids or proteins from a separation medium is effected at a neutral or higher pH.

9 Claims, 4 Drawing Sheets

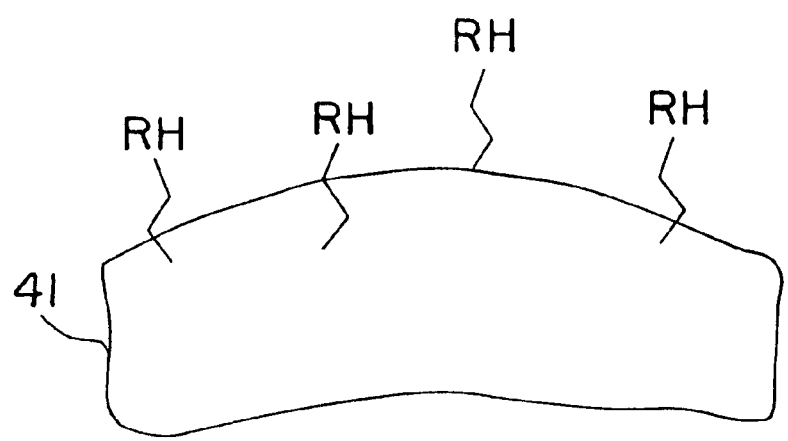
F I G. 4(A)
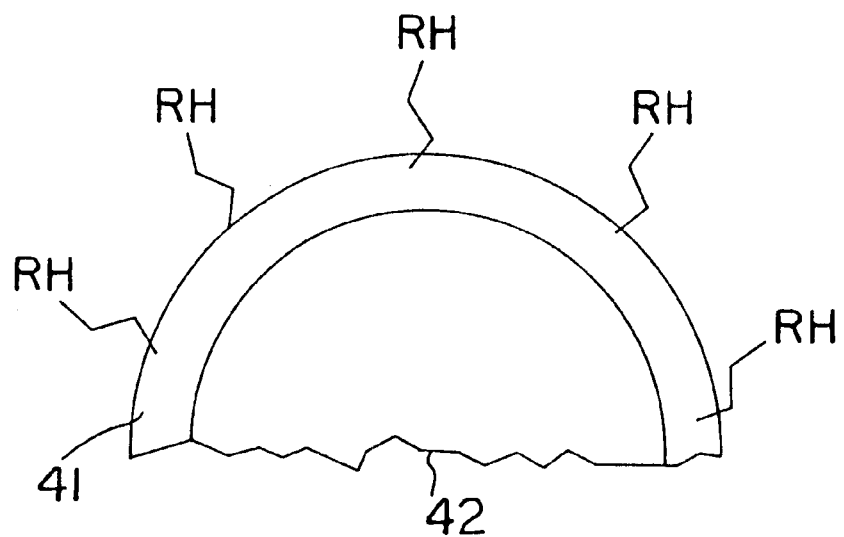
F I G. 4(B)

MATERIALS AND METHODS FOR THE PURIFICATION OF POLYELECTROLYTES, PARTICULARLY NUCLEIC ACIDS

CROSS-REFERENCE TO RELATED APPLICATIONS

This application is a continuation-in-part of U.S. Ser. No. 09/238,343 filed on Jan. 27, 1999, which in turn is a continuation-in-part of U.S. Ser. No. 07/772,346 filed on Oct. 7, 1991, now abandoned.

FIELD OF THE INVENTION

This invention relates to separation and purification of polyelectrolytes. In particular, the present invention relates to the purification of biochemical materials such as proteins and more particularly nucleic acids.

BACKGROUND OF THE INVENTION

Purification of molecular species constitutes a crucial part to their production and utility. This is particularly important in the biotechnology and diagnostics fields. The present invention describes polymeric separation media and methods useful for the purification of molecular species that are polyelectrolytes, such as proteins and nucleic acids. The terms nucleic acid and polynucleotide are used interchangeably, and are used here to signify either a deoxyribonucleic acid (DNA) or a ribonucleic acid (RNA). Unless otherwise specified, the terms polynucleotide and oligonucleotide are used interchangeably.

There is a large body of publications dealing with synthesis, functionalization, and use of ion-exchangers for chromatography and biomolecule purification. (The following patents are herein incorporated by reference in their entirety.) BACKUS et al (U.S. Pat. Nos. 5,582,988 and 5,622,822, and CA 2,157,968) describes a method for isolation of nucleic acids from a lysate by contacting with polymers containing basic groups, such as polyethyleneimine. However, an acidic medium was required for binding, and a strong alkali and heat were found to be the agents most successful in releasing, or eluting, the nucleic acids from the polymer.

COLPAN et al (DE patent number 4139664) describe a method for isolating nucleic acid from cells—by lysis of the cells, then elution of nucleic acid fixed to separation medium surface. However, the method recovers the nucleic acids by eluting with a buffer of high ionic strength.

HENCO et al (DE 3639949) describes a method for the Separation of long-chain nucleic acids—using a porous separation medium to fix the nucleic acids. The invention uses selective salt elution to first wash off the short chain nucleic acids whereas the long-chain nucleic acids are subsequently removed from the anion exchanger using a washing solution of high ionic strength.

SELIGSON and SHRAWDER (U.S. Pat. No. 4,935,342) describe the classical method of isolation of nucleic acids by chromatography on anion exchanger using salt gradients. After the nucleic acids become bound to the ion exchange material and washed, the bound nucleic acids are eluted by passing through the column a salt solution of high molarity.

GANNON (EP 366438) describes the separation of nucleic acid from protein by contacting with cation exchanger at pH below isoelectric point of a protein, i.e., it binds the proteins not the DNA.

Similar principles are offered in U.S. Pat. No. 3,433,782, where selective elution steps effected with varied molarities of LiClO4 or NaClO4.

Similar principles are offered in U.S. Pat. No. 434,324, where purification of deoxyribonucleic acid is accomplished by using anion exchange material, washing with weak ionic salt solution and elution with strong ionic salt solution.

Similar principles are offered by Bourque and Cohen (WO 9514087), where detection of charged oligonucleotides is accomplished by adsorbing on an ion exchange resin, eluting with a high salt buffer and detection. The oligonucleotides bind to the anion exchange resin at 40–65° C., while the desorbing from the resin with a high salt buffer is performed at 40–65°C.

BRUCE et al (Patent Number WO 9411103; GB 9223334) describes magnetizable polymer-based particles derived with ligand having direct binding affinity for nucleic acids etc., for the separation of nucleic acids. The polymer is agarose. The ligand is one capable of assuming a positive charge at pH 7 or below, and is capable of reversibly binding directly to a negatively charged group or moiety in the target molecules. The selected ligands are amines, such as dimethylaminoethyl, and triethanolamine; all have a pKa higher than in our invention.

ADRIAANSE et al (EP 389063 A) describe a method that is widely adapted as diagnostics kits in the art, namely the isolation of nucleic acid using chaotropic agents for nucleic acid binding to solid phase. The use of high concentration of chaotropes, e.g., guanidinium thiocyanate, forces the DNA to precipitate and interact with many surfaces. The present invention avoids the use of highly concentrated chaotropes during purification.

NELSON et al (EP 281390) offered a method for the separation of small nucleotides from larger ones by binding to polycationic support—which does not retain smaller sequences for hybridization assays. The bound nucleic acids were apparently eluted, if needed, by 50% formamide, or other salts.

JP 06335380 A describes a carrier for bonding nucleic acid, which has hybrid-forming base sequence fixed over surface of insoluble solid fine particles. The base of binding is the interaction between complimentary sequences of polynucleotides.

U.S. Pat. No. 4,672,040 also describes a silanized magnetic particles, for use in nucleic acid hybridization, where the principle of binding is the interaction between the hybrid-forming base sequence fixed over surface of insoluble solid fine particles.

MACFARLANE (U.S. Pat. No. 5,300,635), uses quaternary amine surfactants—for isolating nucleic acids from a biological sample by forming complexes which can be dissociated.

HILL (WO 8605815) also describes the use of magnetized nucleic acid sequence comprising single or double-stranded nucleic acid linked to magnetic or magnetizable substance.

HORNES and KORSNES (U.S. Pat. No. 5,512,439) also describe the detection and quantitative determination of target RNA or DNA—by contacting sample with magnetic particles carrying 5'-attached DNA probe.

REEVE (U.S. Pat. No. 5,523,231) describes a method of making a product solution containing a nucleic acid by treating a starting solution containing the nucleic acid by the use of suspended magnetically attractable beads which do not specifically bind the nucleic acid, by precipitating the nucleic acid out of the starting solution in the presence of the suspended magnetic beads whereby a nucleic acid precipitate becomes aggregated with and entraps the beads, followed by separating the precipitate and the entrapped beads and adding a liquid to the precipitate and the entrapped beads to re-dissolve the nucleic acid and re-suspend the beads.

SUMMARY OF THE INVENTION

The present invention is directed to polymeric separation media and to methods useful for the purification of polyelectrolytes, particularly polynucleotides.

In contrast to the prior art methods, the present invention provides mild conditions that avoid the unfavorable, and sometimes harsh conditions otherwise required to bind and elute biomolecules in related art. As mentioned above, prior nucleic acid isolation or purification methods include steps such as heating, and reagents such as strong alkalis, or highly concentrated salts and chaotropes. In addition to being automation and operator unfriendly, these steps/reagents require additional efforts to implement, neutralize, or remove.

The polymeric separation media possess multiple pendant groups, i.e., functional groups, whose protonation state is pH-dependent. Consequently, the amount of charge created on the separation medium can be controlled by adjustment to the pH of the buffer solution where the polymeric separation medium is suspended. As an example, if the pendant groups are basic (B) and possess a pKa of 7, then, at neutral pH (i.e., pH=7), 50% of the groups will acquire positive charges ($BH^+$). Since the pH scale is logarithmic, then, at pH=8, the percent of the positively charged groups will drop to 10%, and to 1% at pH=9. Similarly, if the basic groups possess a pKa of 6, then at pH=9, only 0.1% of the groups will be positively charged, and so forth.

It is an aspect of this invention that at neutral pH, basic groups with pKa as stated above can bind, preferentially strongly, to polyelectrolytes with high negative charge density, such as polynucleotides. At low amount of the positive charges, the separation medium will bind preferably to polyelectrolytes with the most negative charges, such as DNA. Other polyelectrolytes such as proteins, even though they may possess negative charges, will not bind as strongly. The difference in binding strength is attributed to the nature of the charge distribution on polynucleotides and proteins, with polynucleotides possessing multiple, repeated negative charges. As the polymeric separation medium possesses multiplicity of positive charges, even when not totally protonated, multiple electrical interaction (attraction) can occur with the multiple negative charges on the polynucleotides. Bound proteins can be washed off the separation medium by the choice of the pH of the wash buffer. Elution may also be carried in multiple steps, each with an increasing pH, where proteins would elute first, while DNA elutes last. In a preferred embodiment, a negatively charged polyelectrolyte binds to the separation medium at pH 7, as discussed above, and can be eluted in steps with change of the pH to 8 to 10, thus washing off the proteins at pH 8, while eluting DNA at the higher pH. In the above scheme, DNA and protein molecules can be selectively separated form a mixture thereof.

It is an important aspect of this invention, and one of its most preferred embodiments to purify nucleic acids, that the binding step of the positively charged polymeric separation medium occur at a neutral pH where the separation medium is not maximally charged. If the separation medium carries a high positive charge density, then the binding to the highly negatively charged DNA would be too strong to be separated without recourse to harsh conditions, as observed in the prior art listed above.

A purification method using such a separation medium is capable of discriminating between the binding ability of the pH-dependent groups to the different solutes present in a mixture. In addition to selectively binding polyelectrolytes, the separation medium can also selectively elute polyelectrolytes.

Toward operating under mild conditions, an aspect of the present invention is that the pendant groups carry a certain amount of positive charges at neutral pH. It is clear from the discussion above that pendant groups with pKa of about 6 to 7 can bind polynucleotides, and quite strongly at neutral pH. As such, the binding step can thus be accomplished at neutral pH.

In a preferred embodiment, the polymeric separation medium is water-insoluble. In another preferred embodiment, the polymeric separation medium encapsulates a magnetic core, so that it can be separated by the application of a magnetic field.

In another preferred embodiment the polymeric separation medium contains pendant groups that exhibit pKa values of less that about 7, and the medium (buffer) containing the polymeric separation medium is buffered so that the pH of the buffer has a neutral value, thus causing the pendant groups of the polymeric separation medium to be not completely protonated (positively charged) at pH of at least 7.

Preferred pendant basic groups are derived from a base which is a member of the group consisting of pyridine, quinoline, imidazole, and pyrimidine.

Preferred pendant acidic groups are members of the group consisting of a carboxylic group and a phenolic group.

BRIEF DESCRIPTION OF THE DRAWINGS

FIG. 4(A) is a schematic of a polymeric separation medium, 41, provided with pendant groups, RH that are pH dependent. The polymeric separation medium may be one of polysaccharide, silica, or other polymers that can be functionalized to attach the groups. These are acid-base groups, and depending on the ambient pH value, the groups can be protonated, as shown (RH), or deprotonated (R). The groups can be a basic nitrogen, which can be protonated (—$NH^+$) for polynucleotide purification, or the groups can be a deprotonated carboxyl (—$COO^-$) or a deprotonated phenolic (—$C_6H_4$—$O^-$) for the purification of positively charged proteins.

FIG. 4(B) shows a schematic where the polymeric separation medium, 41, surrounds a magnetic core, 42, such as paramagnetic iron oxide.

DETAILED DESCRIPTION OF THE PREFERRED EMBODIMENTS

Figure 1A:
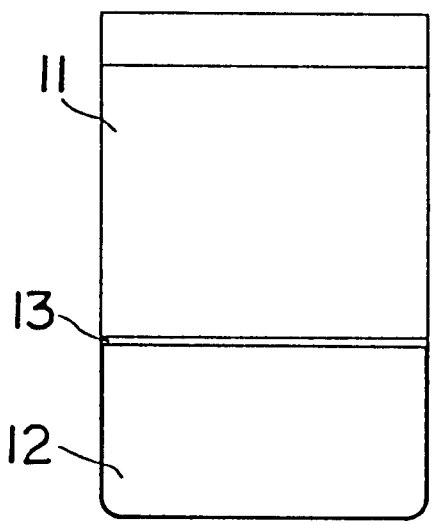
FIGS. 1(A) through 1(D) illustrate the formation of a polymeric medium over a period of time and embodying this invention. The medium is made by slowly adding water, 11, on top of a 2.5% (W/V) agarose solution in 8M urea, 12. A thin layer of gel, 13, which forms at the interface of the agarose and water layers, grows in thickness until all the agarose gels as time progresses from FIG. 1(A) to FIG. 1(D), and as described in Example 1.
Figure 1B:
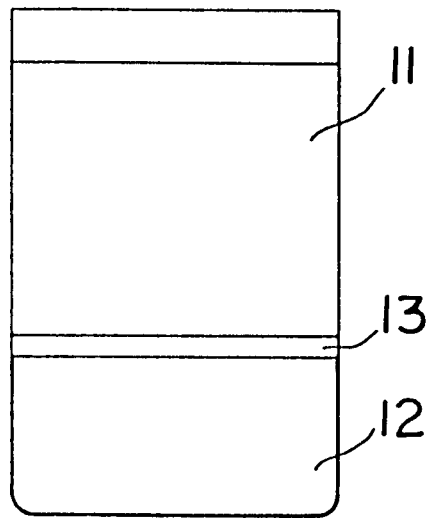
Figure 1C:
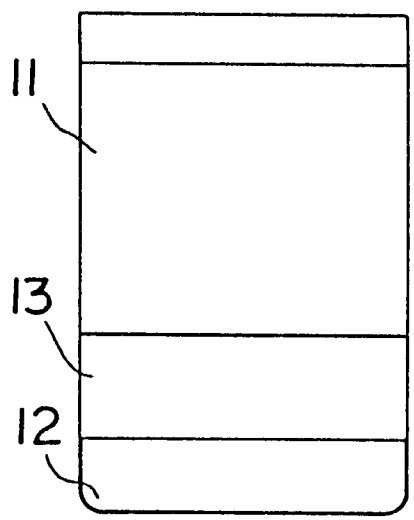
Figure 1D:
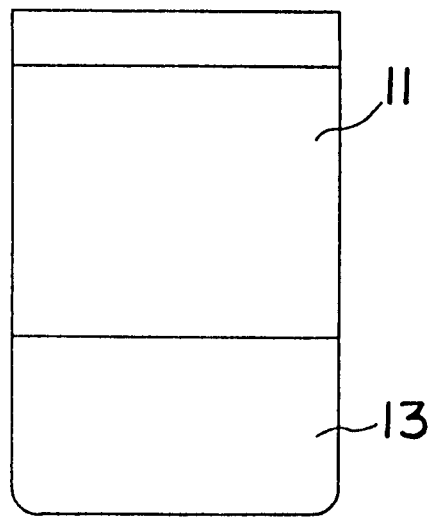

The polymeric separation media possess functional groups that are pH dependent, such as organic acids and organic bases. The pKa of the pH-dependent groups is chosen to be near or slightly below the neutral pH range, e.g., 5 to 7. For organic bases, usually containing nitrogen atoms, the pKa is that of the conjugated acid (base+proton). In the case of organic bases, if the pH is lowered to at or below the pKa, the bases acquire protons to form the conjugate acids. The separation medium thus acquires positive electrical charges, and bind negatively charged polyelectrolytes, such as nucleic acids and negatively charged proteins. The unbound solutes can be separated from the separation medium, and the separation medium can be washed with a low pH buffer. Raising the pH to a value above the pKa of the organic base will force the separation medium to loose its positive charges (protons), and thus release the bound nucleic acids in a pure form.

On the other hand, if the functional group is an organic acid, and the pH is raised to at, or above, its pKa, the separation medium is made to acquire negative electrical charges, and thus binds to positively charged polyelectrolytes, such as positively charged proteins. The unbound solutes can be separated from the separation medium, and the separation medium can be washed with a high pH buffer. Lowering the pH to a value below the pKa of the acidic groups will force the groups to loose their negative charges (by acquiring protons), and thus release the bound polyelectrolytes. Although it is clear from the above discussion that the separation medium can be modified to acquire positive or negative charges by the choice of the functional groups, henceforth, the focus will be on the cases where the separation medium is functionalized with basic groups, to act as nucleic acid purifiers.

In addition to choosing the condition of binding, in this invention, the pKa of the basic groups is chosen to be near or slightly below neutral pH to avoid the harsh conditions that will be required otherwise to release polyelectrolytes, especially biomolecules. When the pKa is around 5 to 7, then polyelectrolytes can bind at pH 7, as discussed above, and can be eluted by a change of the pH to 8 to 10 (weakly basic). This distinguishes this invention from the prevailing methods of purifying proteins and nucleic acids, which employ harsh unfavorable conditions of high salt concentrations and/or highly alkaline solutions to release bound molecules, particularly in the case of nucleic acids purification.

The basic group in a particularly preferred embodiment is p(2-chloroethyl) pyridine (4-picolyl chloride), and similar pyridine, quinoline, imidazole, and pyrimidine derivatives, with near neutral pKa, such as 2-ethyl benzimidazole (6.18), 2-methyl benzimidazole (6.19), 2-phenyl benzimidazole (5.23), isoquinoline (5.42), papaverine (6.4), pyrimidine (6.35), phenanthridine (5.58), p-phenitidine (5.20), 2-picoline (5.97), 3-picoline (5.68), 4-picoline (6.02), pilocarpine (6.87), 2-amino pyridine (6.82), 2-benzyl pyridine (5.13), 2,5-diamino pyridine (6.48), 2,3-dimethyl pyridine (6.57), 2,4-dimethyl pyridine (6.99), 3,5-dimethyl pyridine (6.15), 2-ethyl pyridine (5.89), benzimidazole (5.532), quinoline (4.9), 8-hydroxy quinoline (5.0), 6-methoxy quinoline (5.03), 2-methyl quinoline (5.83), 4-methyl quinoline (5.67), 2-aminothiazole (5.36), p-toluidine (5.08).

For acidic groups, in a preferred embodiment, the groups are carboxylic or phenolic, having a pKa of about 7. Therefore, at pH=8, ninety percent of the groups will acquire negative charges, and thus bind to positively charged polyelectrolytes. In a preferred embodiment, for example, a positively charged polyelectrolyte binds to the separation medium at pH 7, and is eluted by a buffer solution of pH value of about 5 (weakly acidic).

The present invention also describes polymeric separation media suitable for implementing purification, by chemically attaching the above mentioned pH-dependent functional groups to such polymeric separation media, as in FIG. 4(A). In preferred embodiments, the polymeric separation medium is one of polysaccharide, silica, or polyacrylamide polymers. The polysaccharide is preferably an agarose, a dextran, or a cyclodextrin, and derivatives thereof. Typical cyclodextrins are the α-, β- and γ-cyclodextrins. In a preferred method of purification, the sample containing the nucleic acids to be purified is equilibrated with the polymeric separation medium in particulate form (gel particles) carrying pH-dependent groups at pH near the pKa of the groups, where the nucleic acids can preferentially bind to the gel particles. The particles are allowed to separate from the sample solution by gravitational settling or centrifugation, and the unbound solution is aspirated. The particles are washed with a buffer also having a pH near the pKa of the basic groups, and the wash buffer is again aspirated after separation from the particles. The bound nucleic acids may be eluted by a buffer having pH approximately 3 units higher than the pKa of the basic groups, thus releasing the nucleic acids in pure form.

In another preferred embodiment, the above polymeric separation medium surrounds a magnetic core, such as paramagnetic iron oxide particles, as described schematically in FIG. 4(B). For example, magnetic particles may be coated by polymers, using techniques known in the art, to form magnetized separation media in particulate form. The polymer may be subsequently functionalized with pH-dependent groups as discussed herein. In another preferred method of purification, the sample containing the nucleic acids to be purified is equilibrated with the magnetized particles carrying basic groups at a pH near or slightly above the pKa of the groups (e.g., pKa=6, and pH~7), where they preferentially bind nucleic acids. Using a magnet, the particles are separated from the solution. The particles are washed with a buffer, also having a pH near the pKa of the basic groups and the particles are again separated using a magnet, and the wash buffer is aspirated. The bound nucleic acids may be eluted from the particles by a buffer having pH approximately 3 units higher than the pKa of the basic groups, thus releasing the nucleic acids in pure form.

In another embodiment, the separation medium is a gel that pervades the pores of a porous support to form a continuous phase. The porous support is fabricated into a device for the separation using convective flow. The device is formed by imbibing a dissolved, gellable polymer into the pores of the porous support. In a preferred embodiment, the polymer is dissolved by the use of chaotropes. Chaotropes are small solutes that influence the solution behavior of a solvent and its dissolving power. Chaotropes can give the solution the capacity to dissolve polymers that are normally sparingly soluble in the pure solvent. For example, the polymer is a polysaccharide and the chaotrope is urea, guanidinium salts, or KI. In a preferred embodiment, agarose was dissolved in water solution containing 8M urea. This process yields solutions of agarose, which do not gel at room temperature. If water is carefully added to such a solution, a thin gel layer forms at the interface between the agarose solution and the water. The gel layer prevents the migration of the polysaccharide, but still allows further migration of the much smaller urea molecules. As the urea molecules leave the agarose solution into the mainly water medium, the agarose further gels until all the agarose solution turns into gel. The resulting gel can be further chemically modified to attach the pH-dependent groups described above to be used as a separation medium. This process is schematically depicted in FIG. 1(A) through FIG. 1(D), and further explained in Examples 1 through 3.

Figure 2:
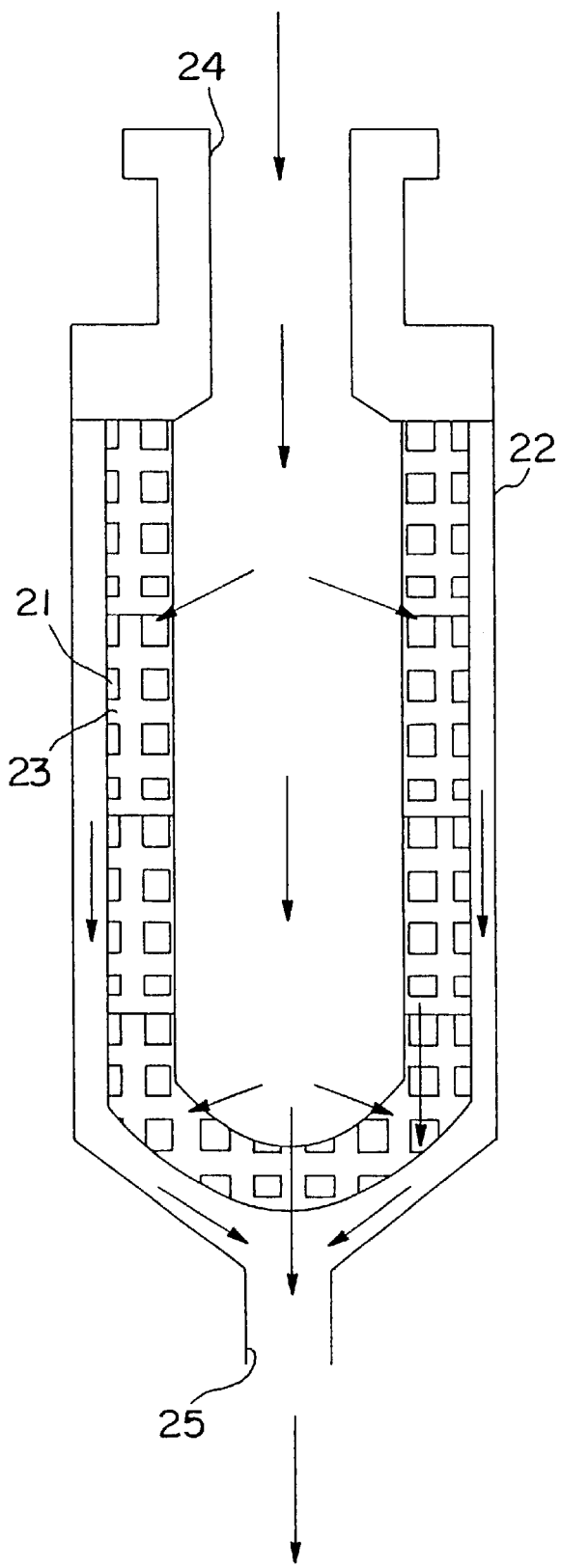
FIG. 2 is a schematic illustration of a cylindrical configuration of a porous support, 21, embodied within an inert casing, 22, after the pores of the support have been impregnated with the gel material, 23, which can be modified to carry pH-dependent groups as in FIG. 4(A). The path of the liquid flow through an inlet port 24, the gel material, 23, and the exit port, 25 is indicated by arrows.
Figure 3:
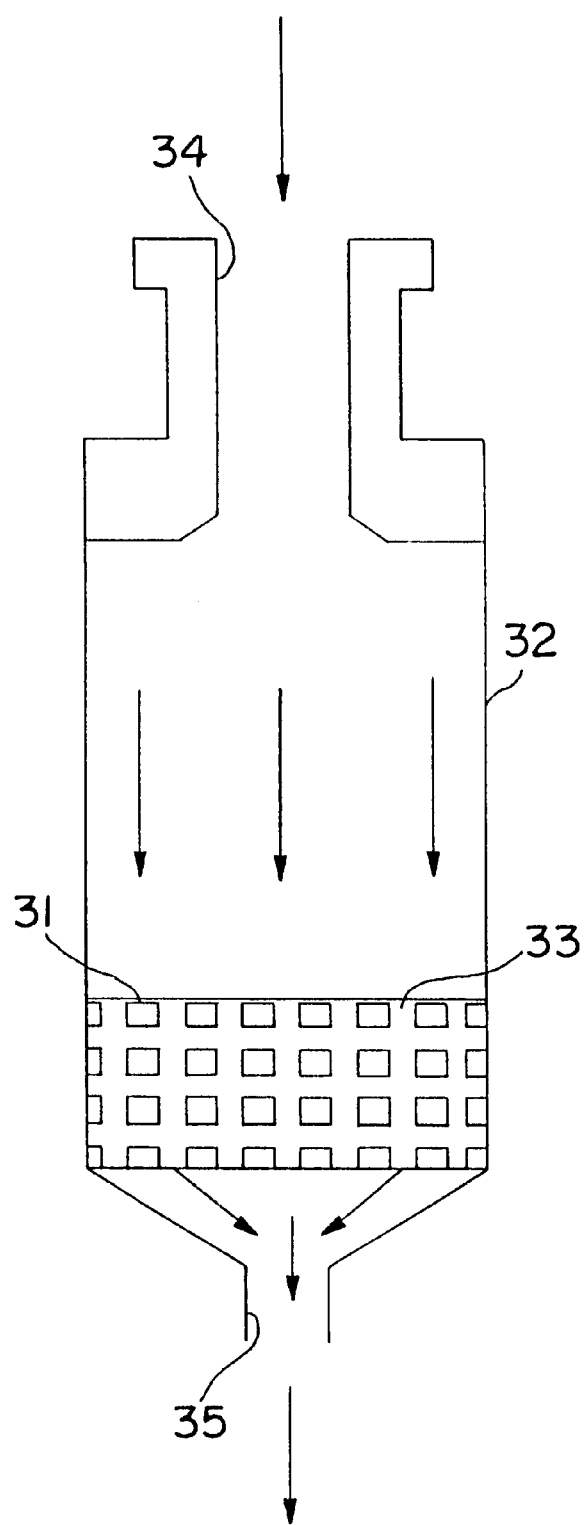
FIG. 3 is a schematic illustration of a flat membrane configuration of a porous support, 31, embodied within a casing, 32, after the pores of the support have been impregnated with the polymeric medium, 33. This medium can be modified to carry pH-dependent groups as in FIG. 4(A), and showing the path of the liquid through an inlet port 34, the gel material, 33, and the exit port, 35.

The porous support can take several forms, preferably a cylindrical shape or a flat shape, as shown in FIGS. 2 and 3, respectively. The polysaccharide solution just described is pushed or drawn by vacuum to impregnate the pores of a porous support, and the excess solution is drained off. The chaotrope (urea) is allowed to migrate from the polysaccharide solution by diffusion through the pores of the support when soaking in water. As the concentration of urea in the pores is lowered, the agarose gels in the pores of the support. The agarose thus becomes entrapped in the pores of the support. This gelling process appears to be unique and gives a stable and reproducible pore-size distribution that is useful for the purpose of this invention. The resulting gel in the above process can be further locked inside the pores by cross-linking of the agarose with a cross-linking agent such as epichlorohydrin and 1,2-dibromo propane.

The porous support material may be made of a number of polymeric, glass, metallic and ceramic materials. In a preferred embodiment, the porous support may be fabricated from ultra high density polyethylene, or polypropylene composition, that is formed into the shape and configuration as shown in FIGS. 2 and 3, which can be obtained from Porex Company, located at Fairburn, Ga.

In another preferred method of purification, the sample containing the nucleic acids to be purified is passed through polymeric separation medium containing basic groups, formed in the pores of the porous support. The process is carried out where the sample and the polymeric separation medium are equilibrated at a pH near or slightly above the pKa of the groups (e.g., pKa=6, and pH~7), whereby the nucleic acids bind to the polymeric separation medium. Wash buffer is then flown to wash off unbound solutes. Wash buffers may have the same pH as the binding buffer (~7). The bound nucleic acids may be eluted by a buffer having pH approximately 3 units higher than the pKa of the basic groups, thus releasing the nucleic acids in substantially pure form.

EXAMPLES

Example 1

25 grams of agarose (Sigma Chemical Co., St. Louis, Mo., product number A9918) were dissolved in one liter of 8M urea solution by heating the solution with stirring until the solution became clear, forming layer 12, in FIG. 1. The medium is made by slowly adding water, 11, on top of a 2.5% (W/V) agarose solution in 8M urea, 12. A thin layer of gel, 13, which forms at the interface of the agarose and water layers, grows in thickness until all the agarose gels as time progresses from FIG. 1(A) to FIG. 1(D), and as described in Example 1. This solution remained ungelled after cooling to room temperature for a period of over 150 days. Upon slow addition of water, layer 11 in FIG. 1, to the top of this solution and standing unperturbed for a few hours, a gelled layer, 13, forms at the interface. This is indicated by the appearance of a white color. This layer plays an important role in preventing further mixing of the water with the agarose in the chaotropic solution. Water and urea molecules can cross this layer, but the agarose molecules, being considerably larger, remain in the bottom layer. At longer times, more urea molecules diffused to the top layer, until the whole bottom part became gelled, as shown in FIGS. 1(A) to 1(D). This solution behavior of agarose was repeated with quantities of agarose concentrations varying from 0.5 to 4% (in 8M urea solution). This solution behavior was also reproduced with 3M NaI solution and buffered 8M guanidine hydrochloride solution. The agarose dissolved to form a clear solution that did not gel at room temperature, however, it became yellowish with time in the case of NaI, presumably due to the oxidation of iodide ions. In the devices that were constructed using this approach, a gelled layer is formed at the surface of the porous support, preventing migration of the entrapped polymer from the pores. The gel structure of the entrapped polymer becomes more predictable as a result of this process.

Example 2

An ultra high molecular weight polyethylene (UHMWPE) porous cylinder, 9.5 mm O.D., 4.8 mm I.D., and 35 mm long was used, with one end sealed and the other open. This cylinder had nominal pore size of 20 microns and void volume (empty space in the walls of the cylinder) of approximately 50%. The inner bore of the cylinder was blocked by a rod of the same diameter as the ID of the cylinder to prevent the agarose solution from filling the bore. Agarose (2.5% w/v) was solubilized in 8M Urea as in Example 1. The agarose solution was vacuum drawn into the pores of the cylinder using a vacuum pump. The cylinder was soaked in water overnight. Referring to the schematic in FIG. 2, this cylinder is numbered 21. The agarose gelled in the pores of the cylinder as the urea diffused out to form the gel, 23. The rod was removed from the cylinder. A luer fitting attachment, 24, was sealed to the open end of the cylinder, and was used to attach the device to syringes or peristaltic pumps for the purpose of processing fluids. The device was placed in a casing, 22. The liquid permeability decreased from approximately 1800 for the gel-free device to about 8 after this step, indicating filling of the pores with the gel.

Example 3

The agarose-filled cylinder in Example 2 was equilibrated in 1M NaOH for 4 hours. The NaOH was drained out and the agarose was cross-linked using 3% epichlorohydrin in 95% (V/V) ethanol/water mixture for 16 hours at room temperature. The resulting cross-linked gel can be used a filtration device. The liquid permeability of the device after cross-linking increased slightly to about 10.

Example 4

The agarose in the cylinder of Examples 3 was allowed to react with 5% (W/V) p-(2-chloroethyl) pyridine (4-picolyl chloride) in 50% (W/V) reagent alcohol-water for 16 hour. This cylinder produced a device with a weak base that is suitable for DNA exchange, since the picolyl group has a pKa of about 6, it can bind DNA at neutral pH's and release DNA at moderately high pH (9).

Example 5

The agarose was cross-linked and re-equilibrated in 10% NaOH in a cylinder as in Examples 2–3. The cylinder was then allowed to react with 10% (W/V) chloroacetic acid in 95% (W/V) reagent alcohol-water for 16 hours. This cylinder produced a device with carboxyl group modified agarose as a weak cation exchanger.

Example 6

The cylinder in Example 5 was equilibrated with 15 mM Tris buffer at pH=7. Aliquots of 5 ml of cytochrome c at 1 mg/ml in the same buffer were loaded through the wall of the cylinder by closing one end of the cylinder. Total protein bound was 32 mg. The cylinder acquired the color of the protein. The device was washed with buffer, and the protein was eluted using aliquots of 500 mM buffered sodium chloride solution. As in Example 5, FIG. 8 shows the bind-elution histogram for cytochrome c.

Example 7

Sephadex G-50 beads (polysaccharide consisting of dextran and cross-linked agarose, Sigma Chemical Co., St, St. Louis, Mo.) were suspended in dioxane and allowed to react with 5% (W/V) p(2-chloroethyl) pyridine (4-picolyl chloride) hydrochloride in 95% (V/V) dioxane-water for 16 hours, with the addition of potassium carbonate as a base. The liquid was aspirated and the beads were washed repeatedly with water until the color disappeared. The beads were functionalized to produce a DNA purifier, since p-ethyl pyridine (gamma picoline) has a pKa of about 6, it can bind DNA at neutral pH's and release DNA at moderately high pH (9). As shown in FIG. 4, the polymeric separation medium may be one of polysaccharide, silica, or other polymers that can be functionalized to attach the groups. These are acid-base groups, and depending on the ambient pH value, the groups can be protonated, as shown (RH), or deprotonated (R). The groups can be a basic nitrogen, which can be protonated (—$NH^+$) for polynucleotide purification, or the groups can be a deprotonated carboxyl (—$COO^-$) or a deprotonated phenolic (—$C_6H_4$—$O^-$) for the purification of positively charged proteins. FIG. 4(B) shows a schematic where the polymeric separation medium, 41, surrounds a magnetic core, 42, such as paramagnetic iron oxide.

Example 8

Approximately 50 mg of the beads in Example 7 were allowed to equilibrate with 0.3 ml of 30 mM acetate buffer of pH=5.5 in an eppendorf tube. 2 microgram solution of DNA (PBKSRV plasmid, from Strategene, ~8 kb in length) in 0.05 ml of water were added to the beads and allowed to incubate at room temperature for approximately 10 minutes with mixing. The beads were centrifuged and the supernatant aspirated. The beads were washed three times with 0.5 ml each of the same buffer, centrifuged, and the buffer was aspirated after each wash. An aliquots of 0.2 ml of alkaline (pH=9) solution of HEPES buffer was added to the beads to elute the bound DNA, and the solution was aspirated. Another 0.5 ml elution step was applied, and again the supernatant was aspirated after centrifugation. After each aspiration step, the aspirated solution was saved for later DNA analysis by gel electrophoresis. Gel electrophoresis results indicate binding of the DNA under the acidic conditions and DNA release under the slightly alkaline elution.

Example 9

Paramagnetic iron oxide beads coated with silica were treated to produce a DNA purifier in a method similar to that in Example 7, by attaching 4-picoline to the silica separation medium.

Example 10

Approximately 50 mg of the magnetic beads in Example 9 were allowed to equilibrate with 0.3 ml of 30 mM acetate buffer of pH=5.5 in an eppendorf tube. 2 microgram solution of the DNA used in Example 8 in 0.05 ml of water were added to the beads and allowed to incubate at room temperature for approximately 10 minutes with mixing. A magnet was brought in contact with the tube, where the magnetic beads were attracted to the side of the tube contacting the magnet, and the supernatant aspirated. The beads were washed three times with 0.5 ml each of the same buffer, and after contacting the tube with the magnet, the buffer was aspirated after each wash. An aliquots of 0.2 ml of alkaline (pH=9) solution of HEPES buffer was added to the beads to elute the bound DNA, mixed and the supernatant aspirated after contacting the tube with the magnet. Another 0.5 ml elution step was applied, and again the supernatant was aspirated after magnetic separation. After each aspiration step, the aspirated solution was saved for analysis. Gel electrophoresis results indicated binding of the DNA under the acidic conditions and complete release of the DNA under the slightly alkaline elution.

Example 11

Approximately 50 mg of the magnetic beads in Example 9 were allowed to equilibrate with 0.5 ml of 30 mM acetate buffer of pH=5.5 in an eppendorf tube. 2 microgram solution of DNA in 0.2 ml of calf serum was added to the beads and the procedure in Example 10 was followed. Gel electrophoresis results indicate binding of the DNA under the acidic conditions and complete release of the DNA under the slightly alkaline elution. The released DNA band in this example was slightly diffuse, presumably due to DNA degradation by the action of nucleases present in the serum, a condition that can be avoided by the addition of a protease or other nuclease-deactivating substances.

I claim:

1. A method for recovery of a DNA polynucleotide from a liquid containing said polynucleotide using a polymeric separation medium which contains 4-picolyl chloride pendant groups exhibiting a pKa value of less than about 7, which method comprises:
   (a) adjusting the pH of the liquid containing the polynucleotide to at least neutral pH and above the pKa of the pendant groups;
   (b) contacting the liquid containing the polynucleotide sample with the polymeric separation medium for a time period sufficient to cause the polynucleotide to form a water-insoluble polynucleotide-separation medium composite;
   (c) separating the liquid from the polynucleotide-separation medium composite;
   (d) washing the polynucleotide-separation medium composite with a buffer solution having at least neutral pH and above the pKa of the pendant groups, and;
   (e) contacting the separate composite with a buffer solution having at least neutral pH and at least 2 pH units above the pKa value of the pendant groups for a period of time sufficient to release the polynucleotide from separation medium.

2. The method in accordance with claim 1 wherein the pH of the liquid containing the polynucleotide is adjusted to decrease the number of positive charges on the pendant groups.

3. The method in accordance with claim 1 wherein the polynucleotide-separation medium composite is washed in multiple steps with buffer solutions of increasing pH values.

4. The method in accordance with claim 1 wherein the polymeric separation medium containing a magnetic substrate and the polynucleotide-separation medium composite is separated from the liquid by the application of a magnetic field.

5. A method for extracting DNA from microorganisms and biological cells present in a biological sample, which method comprises:
   (a) adding a nuclease inactivating substance to said sample in an amount sufficient to inhibit DNA degradation;
   (b) lysing the microorganisms and biological cells in said sample to release the DNA;
   (c) adjusting the pH of the lysed sample to a at least neutral and within about 2 pH units of the pKa of the pendant groups present in step (d);
   (d) contacting the lysed sample with a polymeric separation medium which contains 4-picolyl chloride pendant groups exhibiting a pKa value of less than about 7 for a time period sufficient to cause the DNA to form a DNA-separation medium composite;
   (e) separating the liquid from the DNA-separation medium composite, and;
   (f) contacting the DNA-separation medium composite with a buffer solution having at least neutral pH value and at least 2 units above the pKa value of the pendant groups for a period of time sufficient to release the nucleic acid from separation medium.

6. The method in accordance with claim 5 wherein the pH of the lysed sample containing the DNA is adjusted to decrease the number of positive charges on the pendant groups.

7. The method in accordance with claim 5 wherein the DNA-separation medium composite is washed in multiple steps with buffer solutions of increasing pH values.

8. The method in accordance with claim 5 wherein the polymeric separation medium contains a magnetic substrate and the DNA-separation medium composite is separated from the liquid by the application of a magnetic field.

9. The method in accordance with claim 5 wherein the sample is diluted with a buffer solution having a pH value within about 2 pH units of the pKa of the pendant groups in an amount sufficient to prevent sample coagulation and enhance binding of DNA to the separation medium.

* * * * *